United States Patent

Hammons et al.

[11] Patent Number: 5,957,909
[45] Date of Patent: Sep. 28, 1999

[54] DISPOSABLE ABSORBENT ARTICLE HAVING A RESILIENT MEMBER

[75] Inventors: John L. Hammons, Hamilton; Letha Margie Hines, Cincinnati, both of Ohio

[73] Assignee: The Procter & Gamble Company, Cincinnati, Ohio

[21] Appl. No.: 08/818,761

[22] Filed: Mar. 14, 1997

Related U.S. Application Data

[62] Division of application No. 08/510,356, Aug. 2, 1995, Pat. No. 5,858,011.

[51] Int. Cl.⁶ ..................................................... A61F 13/15
[52] U.S. Cl. ........................................ 604/387; 604/385.2
[58] Field of Search .............................. 604/385.1, 385.2, 604/387

[56] References Cited

U.S. PATENT DOCUMENTS

| | | | |
|---|---|---|---|
| 2,331,355 | 10/1943 | Strongson | 604/385.1 |
| 3,575,174 | 4/1971 | Mogor | 604/385.1 |
| 5,129,893 | 7/1992 | Thoren | 604/385.2 |
| 5,518,801 | 5/1996 | Chappell et al. | 428/152 |

FOREIGN PATENT DOCUMENTS

| | | | |
|---|---|---|---|
| 9103999 | 4/1991 | WIPO | 604/385.1 |
| 9517148 | 6/1995 | WIPO | 604/385.1 |

*Primary Examiner*—Bruce E. Snow
*Attorney, Agent, or Firm*—Larry L. Huston; Jeffrey V. Bamber; J. Daniel Lykins

[57] ABSTRACT

An absorbent article comprises a liquid permeable topsheet; a liquid impermeable backsheet joined to the topsheet; an absorbent core positioned between the topsheet and the backsheet; and a soft resilient member attached to the absorbent core or outside of the core which will preferentially deform, bend or lift in a predictable manner when lateral pressure is applied to the pad, wherein the resilient member consists of at least two distinct pieces of foam.

4 Claims, 6 Drawing Sheets

DISPOSABLE ABSORBENT ARTICLE HAVING A RESILIENT MEMBER

This is a divisional of application Ser. No. 08/510,356, filed Aug. 2, 1995, now U.S. Pat. No. 5,858,011.

BACKGROUND OF THE INVENTION

The present invention relates to a disposable absorbent article which allows better shape retention and body contact during the wearing thereof. More particularly, this invention relates to a catamenial pad having a soft resilient foam member to reduce bunching, densification and collapse. This invention is intended to also cover incontinent articles, sanitary napkins and the like wherein reduced bunching and/or body contact, in addition to comfort, are important to their performance.

It is known that conventional catamenial pads or sanitary napkins comprise a liquid pervious topsheet, a liquid impervious backsheet joined with the topsheet, and an absorbent core for storing fluid positioned between the topsheet and the backsheet. Conventional pads however, have several disadvantages in that when in use, they become bunched through lateral forces from the legs. In addition, conventional cellulosic core matrices may collapse and density due to fluid load and body pressure. The pads thereby become deformed and do not provide a reliable fit or coverage to the undergarments.

Prior known pads have included various structures to try to hold the shape of the pad when in use so that it continues to conform to the shape of the user. Patents which include such structures are described in U.S. Pat. Nos. 4,195,634 to DiSalvo; 4,886,513 to Mason, Jr.; and 5,197,959 to Buell. Although these devices provided structures that could resist certain types of deformation, the search for improved absorbent articles which continue to hold their shape has persisted.

Therefore, it is an object of the present invention to provide a disposable absorbent article which is soft, has a resilient structure, is resistant to wet collapse, and resists densification by body pressures, thereby retaining the shape and reducing bunching. Furthermore, the resilient structure is designed to further reduce bunching and insure sustained body contact of the pad through preferential bending or lift of the pad when lateral forces are applied by the wearer's legs.

SUMMARY OF THE INVENTION

In accordance with the present invention, an absorbent article is provided which comprises a liquid permeable topsheet; a liquid impermeable backsheet joined to said topsheet; an absorbent core positioned between said topsheet and said backsheet; and a soft resilient member attached to said absorbent core which will preferentially deform, bend or lift in a predictable manner when lateral pressure is applied to the pad.

In accordance with a further aspect of the present invention, an absorbent article is provided which comprises a liquid permeable topsheet; a liquid impermeable backsheet joined to the topsheet; an absorbent core positioned between the topsheet and the backsheet, the topsheet, the backsheet and the core forming a product; a substrate backsheet attached to the product at least on a portion of a periphery thereof; and a soft resilient member positioned between the product and the substrate backsheet such that the article will preferentially deform, bend or lift in a predictable manner when lateral pressure is applied to the article.

In accordance with still a further aspect of the present invention, a method of making an absorbent article is provided which comprises the steps of providing a liquid permeable topsheet; providing a shaped absorbent core; providing a piece of tissue; providing a first piece of resilient member having dimensions smaller than the piece of tissue and having a top, a bottom and a side edge; adhering the tissue to the top of the resilient member; folding any remaining tissue over the side edge of the resilient member; cutting at least one additional piece of resilient member; attaching the at least one additional piece to the first piece of resilient member so that the first piece of resilient member drapes over the at least one additional piece of resilient member; attaching a liquid impermeable backsheet to the first piece of resilient member; and sealing the topsheet to the backsheet.

BRIEF DESCRIPTION OF THE DRAWINGS

The invention will now be described by way of example and with reference to the accompanying drawings, in which.

DETAILED DESCRIPTION OF THE PREFERRED EMBODIMENT

Figure 1A:
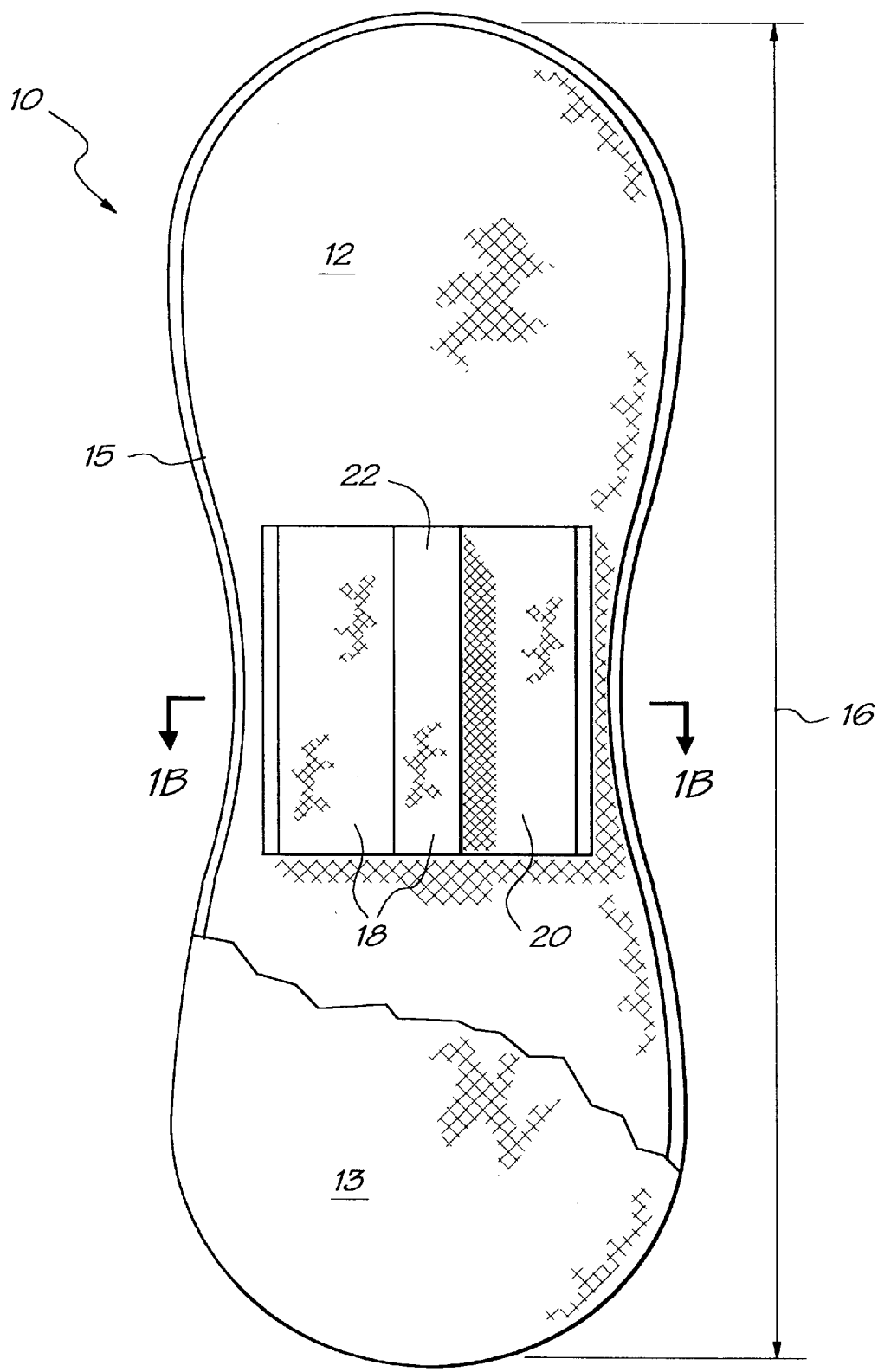
FIG. 1A is a top view of a catamenial pad according to the present invention.

It is an object of the present invention to provide a catamenial pad or other disposable absorbent article having superior fit and fluid handling capabilities by the addition of a resilient member which will preferentially deform, bend, or lift in a predictable manner when lateral pressure is applied to the pad. The pad will bow upwards to contact the body upon lateral compression. When the lateral pressure is released, the pad will spring back out to approximate its full original width.

As used herein, the term "disposable absorbent article" refers to articles which absorb and contain body exudates and more specifically refers to articles which are placed against or in proximity to the body of a wearer to absorb and contain the various exudates which are discharged from the body (e.g., blood, menses, urine) and which articles are intended to be discarded after a single use (i.e. they are not intended to be laundered or otherwise restored or reused). A preferred embodiment of the disposable absorbent article of the present invention would be used in a sanitary napkin or catamenial pad. As used herein the term "sanitary napkin" refers to an article which is worn by females adjacent to the pudendal region and which is intended to absorb and contain menstrual fluids and other vaginal discharges.

In the application of the present invention, a disposable absorbent article such as a catamenial pad is provided which has a liquid pervious topsheet, a liquid impervious backsheet, and an absorbent core. The topsheet and the backsheet preferably have length and width dimensions generally larger than the absorbent core. They are joined together either directly or indirectly through intermediate materials.

The topsheet is compliant, soft feeling, and non-irritating to the wearer's skin. Furthermore, the topsheet is liquid pervious, permitting liquids to readily transfer through its thickness. A suitable topsheet may be made of a wide range of materials such as formed thermoplastic films, apertured plastic films, porous foams, reticulated foams, natural fibers (e.g., wood or cotton fibers), synthetic fibers (e.g., polyester or polypropylene fibers) or from a combination of natural and synthetic fibers with formed films being preferred. Suitable nonwoven topsheets can be an 18 g/yd$^2$ (21.5 g/m$^2$) spunbonded polypropylene nonwoven material known as CELESTRA available from Fiberweb, North America of Simpsonville, S.C., which is then embossed with the pattern described in U.S. Pat. No. 4,781,710 issued to Megison, et al. on Nov. 1, 1988; or the resilient plastic web known as Dri Weave, a plastic apertured formed film such as the macroscopically expanded three-dimensional, resilient plastic web exhibiting a fiber-like appearance and tactile impression made in accordance with U.S. Pat. Nos. 4,342,314 and 4,463,045.

Formed films are preferred for the topsheet because they are pervious to liquids and yet non-absorbent. Thus, the surface of the formed film, which is in contact with the body, remains dry, thereby reducing body soiling and creating a more comfortable feel for the wearer. In addition, the topsheet is sprayed with a surfactant in order to create a hydrophilic surface which helps transfer liquid through the topsheet faster.

The backsheet material is preferably a thin plastic film, though other flexible liquid impervious materials may also be used. The backsheet prevents the exudates absorbed and contained in the core from wetting articles which come into contact with the pad such as pants, pajamas or undergarments. The backsheet thus may comprise a woven or nonwoven material, a polymeric film such as thermoplastic films of polyethylene or polypropylene, or composite materials such a film-coated nonwoven material. An exemplary backsheet material is a 1 mil thick (one thousandth of an inch or 0.025 mm) polyethylene film.

The absorbent core may be formed of any means which is generally compressible, conformable and non-irritating to the wearer's skin, and capable of absorbing and containing liquids and certain body exudates. The absorbent core may be formed in a variety of sizes and shapes (e.g., rectangular, hourglass, etc. as is known in the art) and formed from a wide variety of liquid absorbent materials commonly used in disposable sanitary napkins, diapers and other absorbent articles, such as comminuted wood pulp. This type of wood pulp is generally referred to as airfelt and is utilized in the preferred embodiment of the present invention. Examples of other suitable materials for the absorbent core include cellulosics such as chemically altered cellulosic, thermally bonded cellulosic, superabsorbent hydrogel forming polymer materials which swells when wet (which may, therefore, also be referred to herein as absorbent gelling material or "AGM")—laminates, synthetics, or combinations thereof. Other examples include creped cellulose wadding, absorbent hydrogel materials, polymeric fibers, or any equivalent materials or combinations of materials.

Superabsorbents are materials which are capable of absorbing body fluid in quantities corresponding anywhere from several times to 60 times their own weight. The total absorbent capacity of the absorbent core should, however, be compatible with the design exudate loading for the intended use of the absorbent article. Furthermore, the size and absorbent capacity of the absorbent core may be varied to accommodate the wearer's size and also ranging in the expected amount of exudate fluid volume. For instance, a different absorbent capacity may be utilized for sanitary napkins intended for daytime use as compared with those intended for nighttime use, or for sanitary napkins intended for use by teenage females as compared with those intended for use by more mature women.

The absorbent article of the present invention utilizes a resilient member in order to provide better shape retention and body contact. By using a soft, resilient member with preferential bending or lift, a thin (less than 10 mm caliper and preferably less than 4 mm) absorbent core can be made to provide a catamenial pad which retains its shape, reduces bunching, gives better area coverage and sustains body contact through use. The disposable absorbent article of a first embodiment of the present invention is comprised of a thin absorbent core attached to a resilient foam member positioned between a fluid permeable topsheet and a fluid impermeable backsheet. The original shape and caliper of the core is maintained through use, as a result of the soft, resilient foam member. The resilient member can be made from natural rubber, preferably a cross-linked natural rubber foam or a synthetic material, such as synthetic rubber foam. The member may be attached to the core with adhesive.

It is very important for the core to be thin in order to bend and move with the resilient member as well as to compensate for the added bulk of the resilient member. The sides of the core are thinner than the center and little core material extends beyond the periphery of the member so that only a small area of the pad will be compressed from body pressures during use. This prevents bunching of the entire core and loss of protection. The use of a cross-linked natural rubber foam (XNRF) resilient member provides the unique set of properties of being very flexible and soft but also highly resilient.

Optionally, the core and member may have a tissue cover. A piece of latex bonded airlaid tissue is preferably glued to the foam backbone to help keep the core securely attached to the backbone through better friction and cohesion. The rubber foam alone is very slick and smooth. As a result, the core may become detached and consequently become bunched.

In a preferred embodiment of the present invention, the core is comprised of absorbent gelling material, PET (polyethylene terephthalate) staple fiber (for resiliency) and cellulosic fiber. The core is preferably less than 4 mm, most preferably 3 mm caliper. The tissue is a piece of airlaid tissue, preferably that available from Ft. Howard of Green Bay, Wis. or Merfin of Vancouver, B.C.

This system will now be described in detail below with respect to the figures. It is to be understood that the forgoing general description and the following detailed description are exemplary and explanatory but are not to be restrictive of the invention. The accompanying drawings which are incorporated in and constitute a part of this invention, illustrate the embodiments of the invention, and, together with the description, serve to explain the principles of the invention in general terms. Like numerals refer to like parts throughout the disclosure.

Figure 1B:
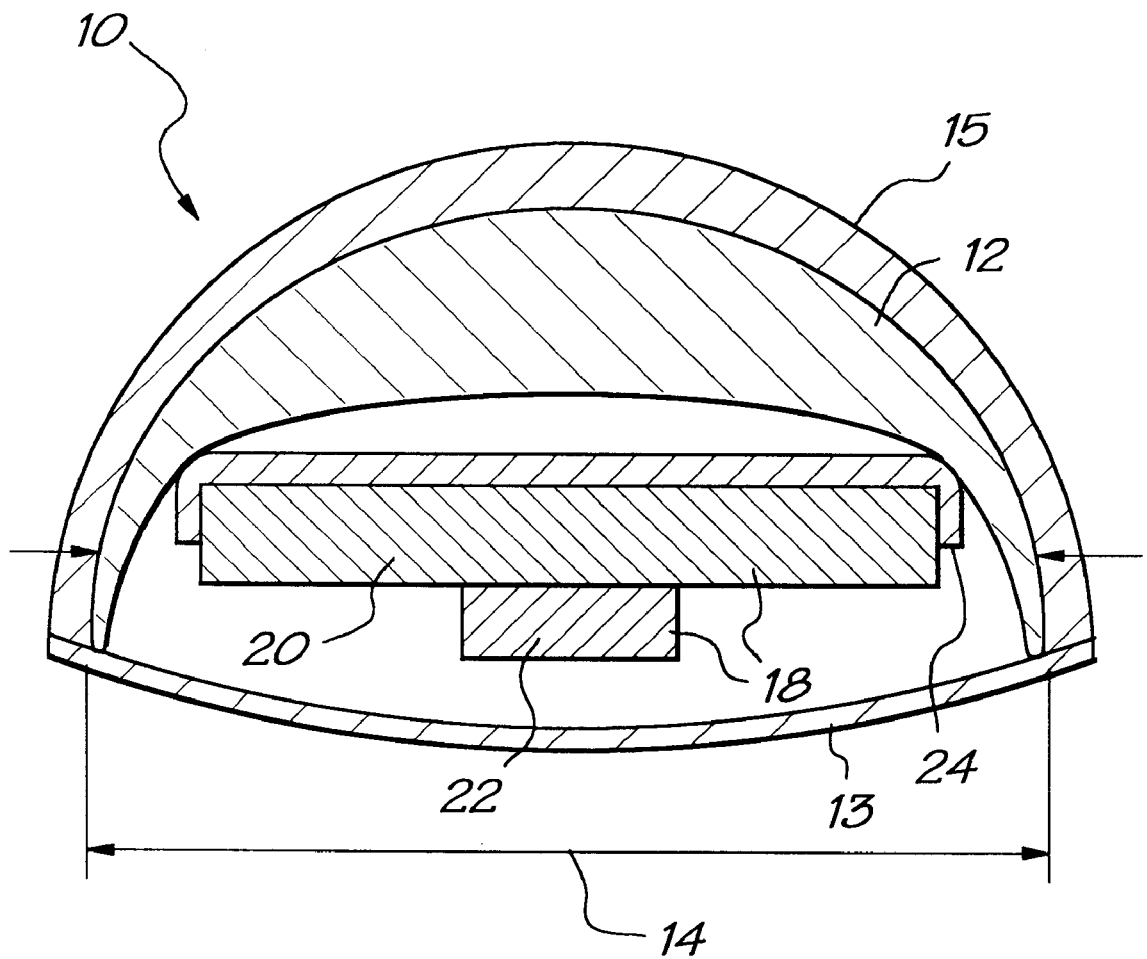
FIG. 1B is an end view of the catamenial pad of the present invention.

The product 10, in accordance with FIGS. 1A and 1B, has an hourglass shape. The core 12 is located between the topsheet 13 and the backsheet 15 and is profiled in the transverse 14 and the longitudinal 16 directions. A two piece resilient member 18 is provided in accordance with the present invention. The first piece 20 is closest to the core 12 and provides full center area coverage. A typical dimension would be 60 mm in width×70 mm in length×2.5 mm in thickness. The caliper of this layer is important so that it is flexible enough to drape over the puck 22 in order to achieve preferred deformation and lift when lateral pressure is applied by the legs. The second piece 22 is a narrow puck. It must have sufficient caliper in order to provide good overall sustained body contact. The majority of the pad caliper is comprised of resilient foam which does not collapse and densify like the current 100% cellulosic core constructions. The puck width must provide the best labial fit but not be intrusive. The puck length must be provided such as not to interrupt gluteal fit (that is, fit in the crevice between the wearer's buttocks). A typical dimension for the puck would be 12 mm in width×70 mm in length×7.5 mm in thickness. The core 12 of the pad 10 is wrapped around the resilient member 18 as shown in FIG. 1(b) to create a longitudinal direction and a transverse-direction profile, similar in shape to a pillow. Specifically, if a product is profiled in the longitudinal direction, it has a thick center and thinner ends. If a product is profiled in the transverse direction, it has a thicker center and thinner sides. This type of profiling improves the absorbency and fit of the product. As stated above, the pad 10 usually includes a tissue 24 glued to the backbone 18 to prevent the core form becoming detached.

The core 12 is preferably made of a blend of cellulosic fibers, absorbent gelling material and PET. The amount of AGM is not as critical as the amount of PET. Preferably, the core is 60–70% cellulosic fibers, about 20% AGM and 10–20% PET. However, as the PET range approaches 20% the core becomes more hydrophobic. Therefore, 10–12% PET is optimal.

In accordance with the present invention, several modifications may be made to this embodiment without departing from the scope of the invention. For example, synthetic rubber foam may be used as a replacement for the XNRF. The dimensions of the insert may be narrowed for an improved fit or to conform to the shape of a wearer. Also, 3 and 4 pieces of foam may be used to build thickness.

Figure 3:
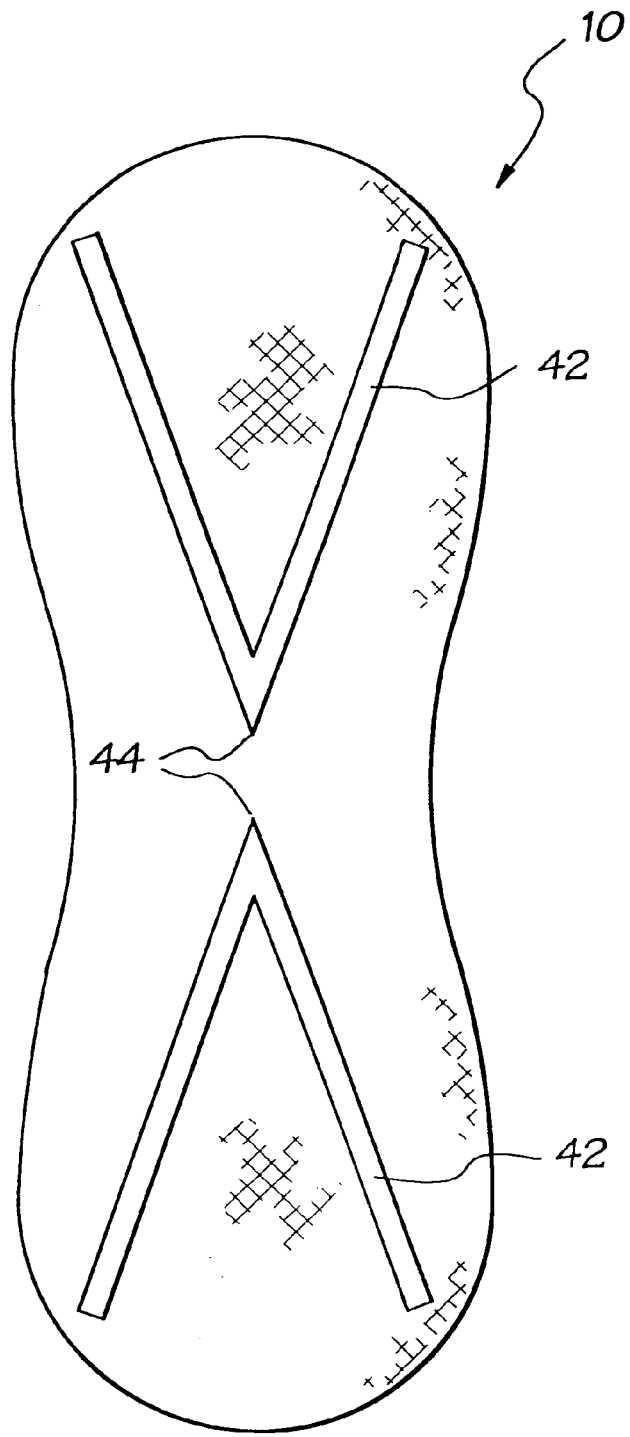
FIG. 3 shows V-shaped panty fastening adhesives.

As shown in FIG. 3, a V-shaped panty fastening adhesive 42 may be used for decoupling the pad 10 for fit at the introitus. In this embodiment, the V-shapes 42 are at both ends of the pad 10 having the pointed portion of the V 44 pointing inward. This is disclosed in WO 93/01783 published Feb. 4, 1993, by Olsen et al. entitled "ABSORBENT ARTICLE FASTENER PATTERN".

As a further alternative, a single piece member design may be incorporated in the design of the present invention in place of a multiple piece construction as long as the member will preferentially deform, bend or lift in a predictable manner when lateral pressure is applied.

In addition to cross-linked natural rubber foam and synthetic rubber foam, numerous types of resilient materials may be used for the resilient member of the pads according to the present invention. These include, but are not limited to, nonwoven highlofts, synthetic fiber batts, scrims (oriented, plastic netting which can be made with varying flexibility) and other forms of foam such as polyurethanes, such as those shown in U.S. Pat. Nos. 5,260,345; 5,263,224 and 5,331,015.

The process of making an absorbent article according to the above-embodiment of the present invention will now be described. Example 1 describes an absorbent disposable article having a resilient cross-linked natural rubber foam member while Example 2 describes an absorbent disposable article having a resilient synthetic rubber foam member.

Method Example 1 (XNRF)

A 7×12 inch (17.8×30.5 cm) piece of continuous topsheet material is ultrasonically bonded to Spunlace, a type of nonwoven material, for the topsheet. An approximately 60×205 mm full-sized shaped core having a composition of 80% airfelt and 20% polyester core blend with 20% a SAN WET absorbent gel material from Sumitomoseilca, Osaka, Japan, is die cut. A partial core having the same material as the full-sized core (0.2 gram per square inch basis weight) and having the dimensions of approximately 60×110 mm is die cut. The partial core is featured into the bottom of the full line made airfelt core blend making a longitudinal profile of the entire core. The top of the core is then bonded to the topsheet using about 0.08 g/pad of adhesive.

Next, an approximately 60 mm×70 mm piece of tissue and an approximately 52 mm×70 mm piece of 0.1 inch (2.5 mm) XNRF foam are cut. These two pieces are then spirally glued together, the Ft. Howard tissue on top of the XNRF foam layer. The extra tissue material is folded over the sides of the XNRF. Two small pieces of 0.2 inch (5:8 mm) XNRF foam having the dimensions of about ½×3 inches (12.7×76.2 mm) are cut out and centered under the larger XNRF layer. They are held in place by one inch tape, preferably 3M tape, placed on the bottom of the small XNRF pieces. A 0.25 inch (6.35 mm) piece of tape is placed down the side of the large XNRF foam and taped to a polymeric backsheet. The topsheet/core and foam subunits are combined before sealing. The resulting pad is die sealed. The pad is then trimmed leaving an approximate 5 mm crimp around its periphery. Then an approximately 2×7 inch (50.8×177.8 mm) panty fastening adhesive is applied to the backsheet. Next, the release paper is applied to the back of the pad. Finally, 0.01 g/pad of surfactant, such as Pegosperse sold by Glyco Chemical, Inc. of Greenwich, Conn., is sprayed on the topsheet to make it hydrophilic.

Method Example 2 (Synthetic Rubber Foam)

A first layer of Ft. Howard tissue is cut having the dimensions of approximately 52 mm×70 mm (2¹⁄₁₆"×2¾"11). Then a top layer of 0.1 inch (2.54 mm) thick rubber foam is cut approximately 52 mm×70 mm (2¹⁄₁₆"×2¾"). Next, three layers of 0.1 inch (2.54 mm) rubber foam are cut having the dimensions of approximately 6.35 mm×76 mm (¼"×3") for the bottom layer. Glue, such as Findley adhesive, from Findley Adhesives, Inc. of Elmgrove, Wis., is applied spirally to one side of the Ft. Howard tissue and the top layer of 0.1 inch (2.54 mm) rubber foam is attached. Then a piece of about 70 mm, 7 inch (25.4 mm) double sided tape is placed down the center of the 0.1 inch (2.54 mm) rubber foam/tissue on the foam side. The paper backing is removed from the 1 inch (25.4 mm) piece of tape. Next, one layer of the 0.1 inch rubber foam (¼×3"(6.35×76.2 mm)) is centered onto the 1" tape. One layer of ¼" (6.35 mm) tape is placed on the foam. Then the paper backing is removed from the tape and another piece of 0.1 inch (2.54 mm) foam is placed on top of the ¼" tape. This process is repeated until all three layers of (¼"×3"(6.35 mm×76.2 mm)) foam are stacked. Next, a piece of ¼ (6.35 mm) tape is placed down the center of the last 0.1 inch foam. A roll of bonded topsheet is cut into approximately 12" (304.8 mm) roll pieces. The topsheet is the embossed CELESTRA as per U.S. Pat. No. 4,781,710, layered with a Dry Weave material, as shown in U.S. Pat. No. 4,919,738 to Ball et al., entitled "DYNAMIC MECHANICAL BONDING METHOD AND APPARATUS". The topsheet (Dry Weave side down) is placed onto the work surface. Core bonding adhesive, such as Findley H2031- 0.005 g/in$^2$ (0.0323 g/cm$^2$), a hot melt adhesive, was applied to the CELESTRA side of the topsheet. The release paper is then removed from the adhesive. The 64% airfelt, 16% PET (CELWET from Hoescht Celanese), 20% AGM core was placed carefully centered on the spiral glue. The synthetic rubber foam unit is placed onto the back side of the core having the Ft. Howard tissue side towards the core. The unit is centered in the longitudinal and transverse directions. The paper backing is removed from the 3 pieces of the ¼" (6.35 mm) tape on the last piece of foam. A polyethylene backsheet is applied. The pads are then sealed with a die. Panty fastening adhesive having the dimensions of about 2"×¾" (50.8 mm×19.05 mm) is applied in a "V" shaped pattern on white release paper. The pad is then strayed with a surfactant, such as Pegosperse (0.01 g/pad). Finally, the article is inspected.

The article had the following finished product dimensions:

| | |
|---|---|
| weight | 12.5 g |
| length | 225 mm |
| center width | 76 mm |
| end width | 93 mm |
| center caliper | 20.2 mm |
| end caliper | 8.4 mm |

Besides the above arrangement of a resilient member and puck arrangement, other dimensions of the insert may provide additional benefits for fit. For example, the resilient layer could be placed outside the backsheet and/or enclosed by a layer of polymeric material. Or, the resilient member may be glued to the base for a more secure attachment.

Additionally, products such as a core tube or bun as shown in U.S. Pat. No. 4,425,130 to Des Marais, could be used in conjunction with the resilient member insert. A bun is a tufted bundle of capillary channel fibers that are positioned generally on top of the absorbent core. Products with very flexible ends could be used to enhance fit in the gluteal groove.

For example, in accordance with an alternative embodiment of the present invention, the absorbent core may be superimposed onto an adhesive which is applied to the inner surface of the backsheet and which is intended to hold the barrier sheet in place on the absorbent core. In this embodiment, the topsheet extends around the side edges of the absorbent core and over the barrier sheet where it overlaps itself on the garment surface of the napkin so as to completely envelope the element. The absorbent core, and the barrier sheet thereby form what is commonly known as a "tubular napkin". The overlapping portions of the topsheet and the barrier sheet are heat-sealed to each other to form the end edges of the napkin. Three of these arrangements will be described hereinbelow and with respect to FIGS. 2A–2C.

Figure 2A:
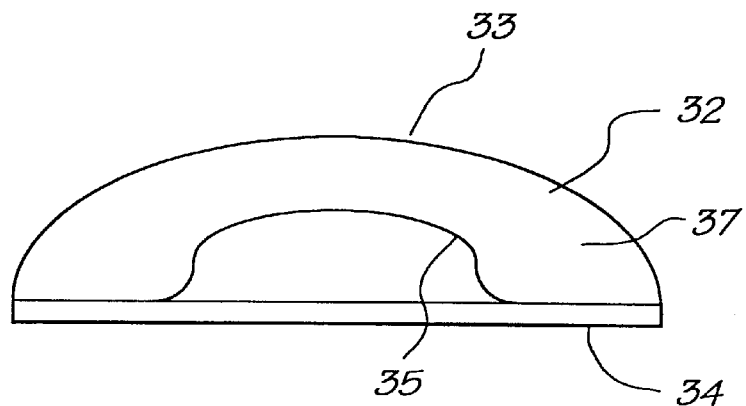
FIGS. 2A–2C are end views of three alternative pad designs.

In the first arrangement shown in FIG. 2A, the tube 32 comprises the entire pad including the topsheet 33, backsheet 35 and absorbent core 37. The tube 32 is attached with double sided tape to a structural elastic-like polymer film backsheet 34. The polymer film backsheet 34 need not provide all of the functions of a backsheet and need not extend the entire length of the pad. Its purpose is to provide the deformation of the core 37 for improved fit.

Figure 4A:
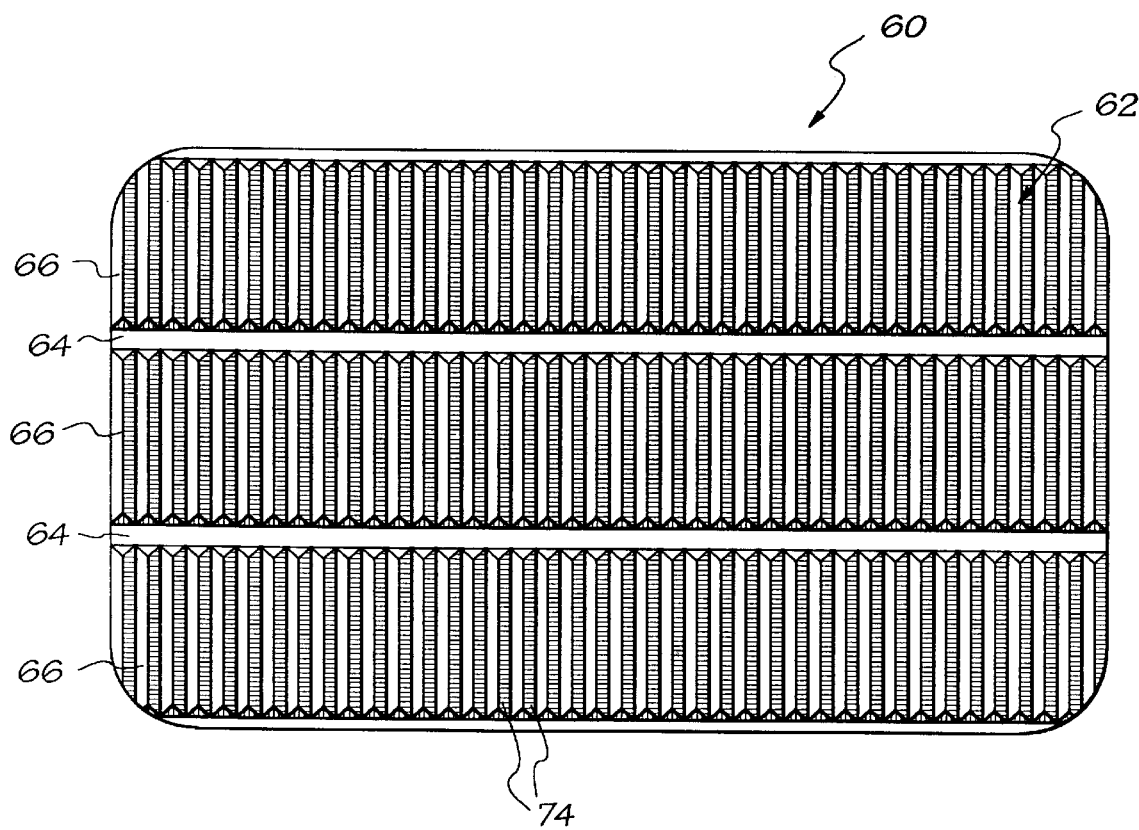
FIGS. 4A–4D show simulated elastic-like polymer film which is used in a preferred embodiment of the present invention.
Figure 4B:
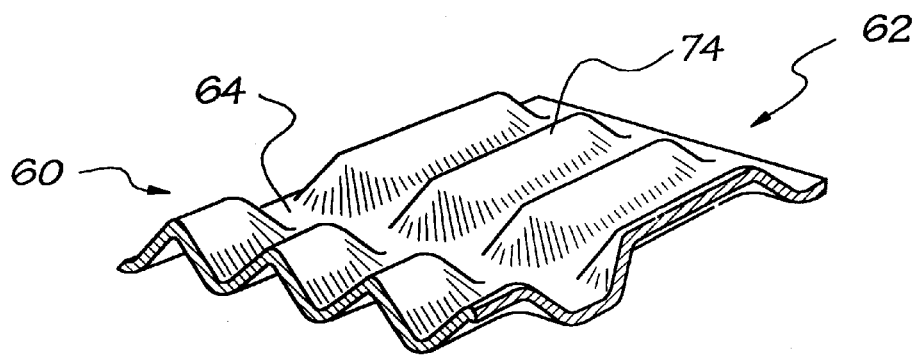
Figure 4C:
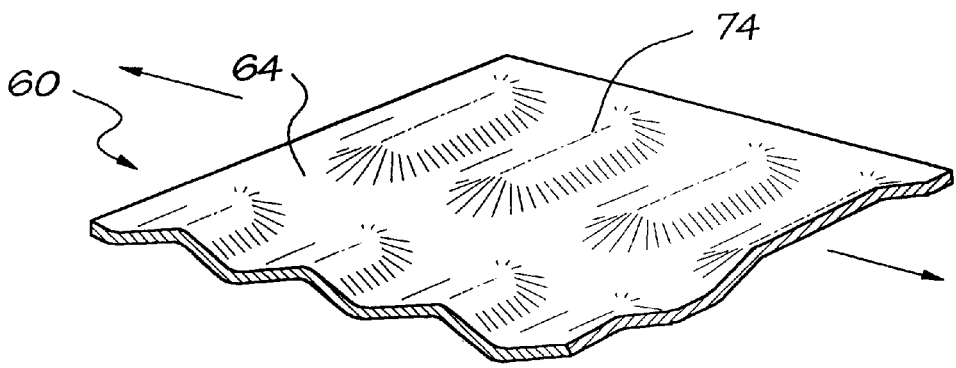
Figure 4D:
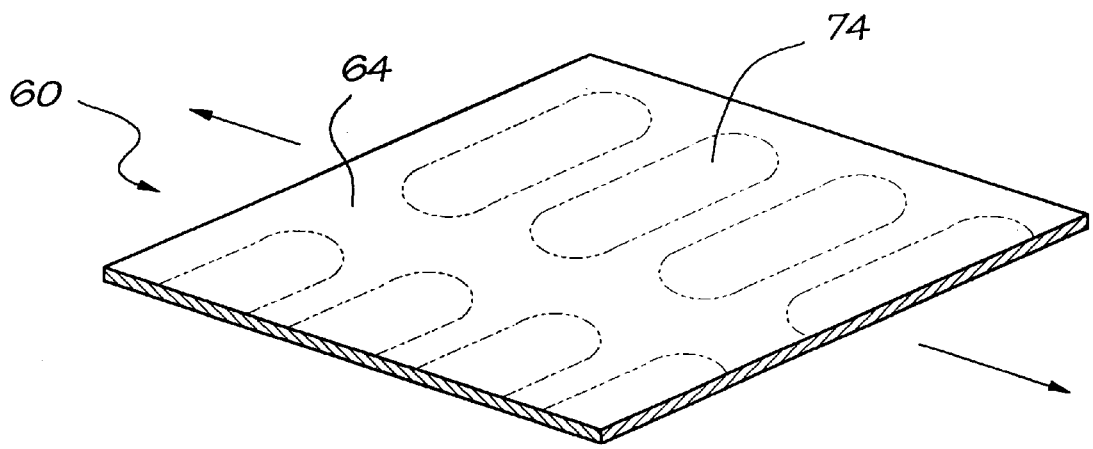

Such a structural elastic-like polymer film is defined as shown in FIGS. 4A–4D. A web of material 60 is shown having a network 62 of strainable regions formed therein that exhibit an elastic-like behavior in the direction of elongation without the use of added elastic materials. Two distinct regions provide the web with a first region 64 of a elastic-like, relatively low resistive force stage and a second region 66 of a relatively high resistive force stage. The second region 66 includes a plurality of continuous, interconnected deformations 74 which extend beyond the plane of the first region 64. FIGS. 4B–4D show the manner in which the structural elastic-like polymer strainable web material 60 exhibits at least two significantly different stages of controlled resistive force to elongation when subjected to an applied elongation.

Figure 2B:
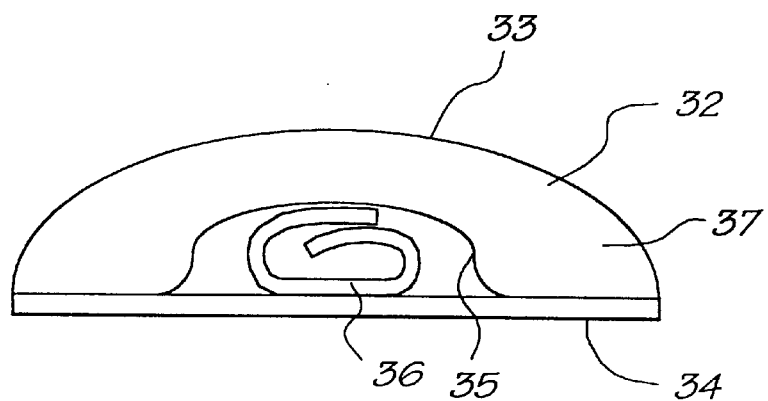
Figure 2C:
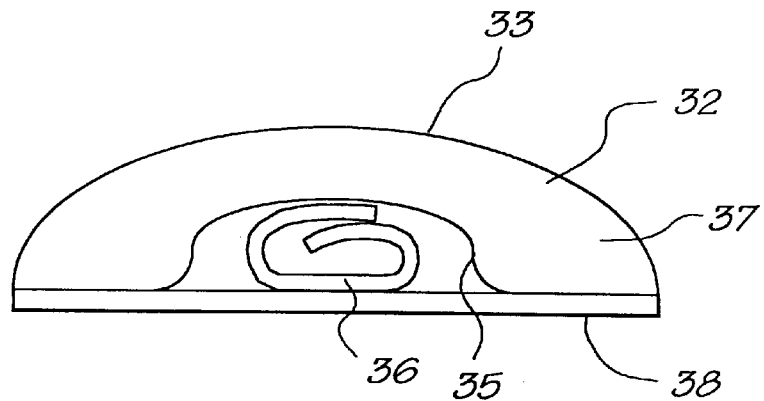

In the second alternative arrangement, the tube 32 is attached as above. However, in addition, a XNRF resilient member roll 36 is inserted in the tube 32 as seen in FIG. 2B. The XNRF is preferably approximately 5 mm thick and approximately 65 mm in length. The roll 36 may be further secured to the polymer film backsheet 34 with glue, if desired. The resilient member roll 36 is outside of the main backsheet 35 and therefore, no tissue is required to attach the roll 36 to the core 37.

In the third arrangement, the resilient XNRF roll 36 is inserted in the tube 32 as in the second arrangement above. However, in place of the structural elastic-like polymer film as a backsheet 34, an approximately 2 mm thick layer of XNRF 38 is used, which preferably has the dimensions of approximately 70 mm by 50 mm, as shown in cross-section in FIG. 2C.

Therefore, it is seen from the above embodiments that the addition of a resilient member 36 enhances the fit and fluid handling capabilities of a disposable absorbent article.

Having described the invention in detail and by reference to preferred embodiments thereof, it will be apparent that modifications and variations are possible without departing from the scope of the invention defined in the appended claims.

What is claimed is:

1. An absorbent article having a predetermined shape comprising:

a liquid-permeable topsheet;

a liquid-impermeable backsheet joined to said topsheet;

an absorbent core positioned between said topsheet and said backsheet, wherein said core is adhered to an inner surface of said backsheet such that said backsheet is held in place on said absorbent core, said topsheet, said backsheet and said core forming a product; and a substrate backsheet joined to said product at least on opposing longitudinal portions of a periphery thereof forming a cavity between said product and said substrate backsheet, said product being deformed upwards in a predictable manner when pressure is applied to said article by a wearer, and returned to approximate said predetermined shape when said pressure is released;

wherein said substrate backsheet is a structural elastic-like polymer film having a network of distinct strainable regions formed therein that exhibit an elastic-like behavior without the use of added elastic materials.

2. The absorbent article of claim 1 wherein said article further comprises a resilient member, said resilient member being rolled and positioned between said product and said substrate backsheet wherein said resilient member enhances fit and fluid handling capabilities of said article.

3. The absorbent article of claim 2 wherein said resilient member is a crosslinked natural rubber foam.

4. The absorbent article of claim 1 wherein said substrate backsheet is joined to said product using double sided tape.

* * * * *